United States Patent
Billings et al.

[11] Patent Number: 6,128,518
[45] Date of Patent: Oct. 3, 2000

[54] SYSTEM AND METHOD FOR IN-VIVO HEMATOCRIT MEASUREMENT USING IMPEDANCE AND PRESSURE PLETHYSMOGRAPHY

[75] Inventors: Robert Gail Billings; Justin S. Clark, both of Salt Lake City; Ke-shieng Yang, Sandy; Jon Neese; Allan L. Kaminsky, both of Holladay, all of Utah

[73] Assignee: Microcor, Inc., Salt Lake City, Utah

[21] Appl. No.: 09/121,000

[22] Filed: Jul. 23, 1998

Related U.S. Application Data

[63] Continuation-in-part of application No. 08/885,747, Jun. 30, 1997, abandoned, which is a continuation of application No. 08/602,700, Feb. 16, 1996, Pat. No. 5,642,734, which is a continuation-in-part of application No. 08/425,404, Apr. 20, 1995, Pat. No. 5,526,808, which is a continuation of application No. 08/298,795, Aug. 31, 1994, abandoned, which is a continuation of application No. 08/114,131, Aug. 30, 1993, abandoned, which is a continuation of application No. 07/592,851, Oct. 4, 1990, abandoned

[60] Provisional application No. 60/057,166, Aug. 28, 1997.

[51] Int. Cl.[7] ........................................................ A61B 5/05
[52] U.S. Cl. .......................... 600/345; 600/506; 600/547
[58] Field of Search ..................................... 600/345, 363, 600/506–507, 547

[56] References Cited

U.S. PATENT DOCUMENTS

| | | |
|---|---|---|
| 5,111,817 | 5/1992 | Clark et al. . |
| 5,277,181 | 1/1994 | Mendelson et al. ................ 600/322 X |
| 5,526,808 | 6/1996 | Kaminsky . |
| 5,642,734 | 7/1997 | Ruben et al. . |

*Primary Examiner*—Samuel G. Gilbert
*Assistant Examiner*—Ryan Carter
*Attorney, Agent, or Firm*—Trask, Britt & Rossa

[57] ABSTRACT

The hematocrit of blood (i.e., the percentage of whole blood volume occupied by red blood cells) perfusing a finger is determined by stimulating the finger with two current frequencies, one relatively high (e.g., 10 MHZ) and the other relatively low (e.g., 100 KHz). Voltages induced in the finger in response to the two current frequencies are then captured and separated into baseline and pulsatile components. The hematocrit is determined as a function of the ratio of the high frequency pulsatile component to the low frequency pulsatile component, multiplied by the ratio of the square of the low frequency baseline component to the square of the high frequency baseline component. The signal-to-noise ratio of the captured voltages can be enhanced by the application of external pressure to the finger, such as by applying a pressure cuff to the finger.

30 Claims, 3 Drawing Sheets

SYSTEM AND METHOD FOR IN-VIVO HEMATOCRIT MEASUREMENT USING IMPEDANCE AND PRESSURE PLETHYSMOGRAPHY

This application claims the benefit of a U.S. Provisional Application filed Aug. 28, 1997, entitled "Device and Method for In-Vivo Hematocrit Measurement Using Impedance and Pressure Plethysmography," having application Ser. No. 60/057,166, now pending, and is also a continuation-in-part of a patent application filed Jun. 30, 1997, entitled "Method and Apparatus for Noninvasively Determining Hematocrit," having Ser. No. 08/885,747, now abandoned, which is a continuation of a patent application filed Feb. 16, 1996, having Ser. No. 08/602,700, now U.S. Pat. No. 5,642,734, which is a continuation-in-part of a patent application filed Apr. 20, 1995, having Ser. No. 08/425,404, now U.S. Pat. No. 5,526,808, which is a continuation of a patent application filed Aug. 31, 1994, having Ser. No. 08/298,795, now abandoned, which is a continuation of a patent application filed Aug. 30, 1993, having Ser. No. 08/114,131, now abandoned, which is a continuation of a patent application filed Oct. 4, 1990, having Ser. No. 07/592,851, now abandoned.

BACKGROUND OF THE INVENTION

1. Technical Field

This invention relates in general to devices and methods for in-vivo measurement of blood hematocrit and, more specifically, to devices and methods for such measurement that use impedance and pressure plethysmography.

2. State of the Art

The "hematocrit" of blood, which is defined as the percentage of whole blood volume occupied by erythrocytes (i.e., red blood cells), is an important measure of patient well-being in cases of trauma, blood loss by disease, iron depletion in pregnancy, dietary iron deficiency, and a number of more specific medical conditions.

Hematocrit has traditionally been measured by centrifuging a column of blood, which has been extracted from the patient, in a glass tube, until the erythrocytes are compacted by centrifugal force to one end of the tube. The hematocrit is determined by measuring the length of the tube containing dark red material and dividing by the total length of the liquid column in the tube. These length observations are usually made visually, but are also made, in some cases, by automated optical means of various designs. Besides centrifugal hematocrit determinations, hematocrit is also derived and reported by various automated blood analyzers which count erythrocytes optically in unpacked blood. This erythrocyte count correlates with packed cell hematocrit and the derived hematocrit is reported.

It is noted that the methods of obtaining hematocrit described above are invasive, that is, they require that blood be removed from the patient in order to determine the hematocrit. A non-invasive method would be desirable because it would subject the patient to less pain and inconvenience and would preserve the patient's blood for its normal functions.

It has long been recognized by biomedical researchers that the electrical impedance of blood varies with hematocrit and that, as a result of this relationship, it should be possible to derive hematocrit from the measurement of blood impedance. This has been successfully done on blood which has been extracted from the patient and placed in an impedance measuring cell of controlled dimensions, where the blood is stationary, maintained at a known temperature, and agitated to maintain uniform cell distribution. Examples of such successful measurements are given by Okada and Schwan in "An Electrical Method to Determine Hematocrits," IRE Transactions in Medical Electronics, ME-7:188–192 (1960) and by deVries et al. in "Implications of the Dielectrical Behavior of Human Blood for Continuous Online Measurement of Hematocrit," Medical & Biological Engineering and Computing, pp.445–448 (1993). Like the centrifugal methods, these methods are invasive, however, and thus do not satisfy the need for a non-invasive hematocrit measurement. The impedance methods have, however, provided the inspiration for some ingenious inventions to measure hematocrit in-vivo and non-invasively.

The first in-vivo impedance measurement of hematocrit known to the inventors was reported by Yamakoshi et al. in "Noninvasive Measurement of Hematocrit by Electrical Admittance Plethysmography Technique, " IEEE Transactions, BMB-27, 3:156–161(1980). This measurement was made by immersing the finger of the test subject in a saline solution contained in a chamber fitted with impedance measuring electrodes. The electrolyte concentration of the saline solution was then varied by mixing in either water or more concentrated saline until the pulsatile variations of impedance caused by the increased volume of blood on each pulse were minimized. When this minimization of pulses occurred, the saline solution had the same resistivity as the blood in the pulsing arteries and this resistivity could be correlated against the known, previously determined relationship between resistivity and hematocrit.

U.S. Pat. No. 5,526,808 by Kaminsky, assigned to Microcor, Inc., the assignee of the present invention, describes another impedance method for measuring hematocrit non-invasively and in-vivo. This method draws upon the observation that hematocrit determines the frequency vs. impedance profile of blood. In addition, the method of the '808 patent uses the pulsatile change of impedance in a finger or other limb of the body that occurs when each heartbeat pushes new blood into the organ where the measurement is made to separate the non-blood tissue impedance from the blood impedance.

The mathematical model upon which this method is based relies upon the assumption that the admittance (i.e., the reciprocal of impedance) change that occurs when blood pulses into the finger or other limb where the measurement is being made is due to the increased volume of blood providing a new current path in parallel with the old current path present before the pulse occurs. Thus, the difference in admittance between baseline, when no new blood is in the limb, and during the pulse, when new arterial blood has entered the limb, is due to the new blood, and the numerical value of this admittance difference is proportional to the volume of the new blood times the admittance of the new blood.

As shown in devries et al., the admittance vs. frequency characteristics of blood have a characteristic shape that depends upon hematocrit. Comparing the shapes of either the magnitude or the phase versus the frequency of the admittance, derived for the pulsed blood, against known characteristic hematocrit-dependent shapes gives a measure of hematocrit. The known characteristic shapes can be derived from a database obtained from patients having hematocrits independently measured by the centrifugal method previously described.

U.S. Pat. No. 5,642,734 to Ruben et al., assigned to Microcor, Inc., assignee of the present invention, describes some additional methods to obtain in-vivo hematocrit results. First, the '734 patent describes using pressurized cuffs, in various ways, to change the amount of blood in the organ (e.g., the finger) under measurement. Second, the '734 patent describes a unique electronic system for driving electrodes attached to the body part under measurement and for deriving phase as well as amplitude information from impedance measurements of the body part. Third, the '734 patent teaches the use of a neural network computer algorithm to relate measured impedance and other data to hematocrit based upon matching a database obtained from a number of prior measurements of patients with separately-determined hematocrits.

In the field of blood oxygen saturation measurement, as opposed to the field of blood hematocrit measurement that has been under discussion thus far, U.S. Pat. No. 5,111,817 to Clark et al. observes that the accurate measurement of blood oxygen saturation levels in arteries ($S_aO_2$) in a body part under measurement, such as a finger, is typically hindered by different blood oxygen saturation levels in capillaries ($S_cO_2$) in the body part. Clark et al. teaches a method for correcting measurements of $S_aO_2$ for the effects of $S_cO_2$. In this method, a pressure cuff applies a pressure to the body part under measurement that is equal to the mean arterial blood pressure in the body part. As a result, measurements from the body part are dominated by the effects of the actual $S_aO_2$ in the body part, so that the measured $S_aO_2$ is closer to the actual $S_aO_2$.

SUMMARY OF THE INVENTION

A system in accordance with this invention for measuring the hematocrit of blood perfusing a living body part (e.g., a finger) includes circuitry that drives first and second alternating currents of different frequencies (e.g., 100 KHz and 10 MHz) between separate points on the body part. The alternating currents may be applied to the body part through input electrodes attached to the body part at the separate points. Also, additional circuitry monitors first and second signals (e.g., voltage waveforms) induced in the body part by the first and second currents (e.g., by monitoring output electrodes attached to the body part), and other circuitry generates first and second pulsatile signals and first and second baseline signals from the first and second induced signals. Determining circuitry then calculates the hematocrit of the blood from the first and second pulsatile signals and the first and second baseline signals. This calculation may be performed, for example, by determining the hematocrit (H) from the following equation:

$$[(1+(f-1)H)/(1-H)]\{1+[((af(e^{-bx}-c))x/(1-x))-1]H\}/\{1+[((af(e^{-bx}-c))/(1-x))-1]H\}=C\cdot(\Delta Volt_H/V_H^2)/(\Delta Volt_L/V_L^2),$$

where f, a, b, x, c, and C are various constants, as will be described below, $\Delta Volt_H$ and $\Delta Volt_L$ are the first and second pulsatile signals, and $V_H$ and $V_L$ are the first and second baseline signals.

In accordance with another embodiment of this invention, a system for measuring the hematocrit of blood perfusing a living body part includes electrodes positioned on the surface of the body part. A measuring device measures the electrical impedance at one or more frequencies between the electrodes. Also, a chamber is positioned to surround the body part between the electrodes, and a measuring apparatus measures pulsatile blood volume by the pulsatile-related change in internal pressure within the chamber. Further, a calculating device (e.g., a programmed microprocessor) determines the blood hematocrit from the measurements of impedance and pulsatile blood volume. The device may determine the hematocrit H in accordance with the following equations:

$$H=(\rho-58)/(0.01\rho+0.435),$$

and $$\rho=\Delta VZ_0^2/L^2\Delta Z,$$

where $\Delta V$ is the change in pulsatile blood volume at any point in time, $\Delta Z$ is the change of impedance at the same point in time, L is a constant which will be described below, and $Z_0$ is the baseline impedance at the beginning of each pulse.

In a further embodiment of this invention, a system for determining blood hematocrit includes circuitry that produces a current signal including a first, relatively low frequency portion and a second, relatively high frequency portion, and a device that stimulates a living body part containing blood with the current signal. Also, additional circuitry senses voltages at the first and second frequencies induced in the body part by the stimulation thereof, and further circuitry detects signal envelopes of the sensed voltages, with each signal envelope having a pulsatile component and a baseline component. Isolation circuitry isolates the pulsatile components and baseline components of the detected signal envelopes, and extraction circuitry extracts one or more sets of time-matched segments of the isolated pulsatile components and one or more sets of time-matched segments of the isolated baseline components. Further, other circuitry effectively correlates the blood hematocrit to the product of the ratio of the time-matched segments of the pulsatile components and the inverse ratio of the squares of the time-matched segments of the baseline components.

In an additional embodiment of this invention, an apparatus for determining the hematocrit of blood perfusing a living body part from relatively low frequency pulsatile and baseline signals induced in the body part, and from relatively high frequency pulsatile and baseline signals also induced in the body part, includes circuitry that effectively determines the ratio of the product of the relatively high frequency pulsatile signal and the square of the relatively low frequency baseline signal to the product of the relatively low frequency pulsatile signal and the square of the relatively high frequency baseline signal. The apparatus also includes circuitry that correlates the blood hematocrit to the effectively determined ratio.

Other embodiments of the invention include methods of measuring the hematocrit of blood perfusing a living body part, and a method of determining blood hematocrit, that generally correspond to the systems and apparatus described above.

DETAILED DESCRIPTION OF THE ILLUSTRATED EMBODIMENTS

The disclosures of U.S. Pat. Nos. 5,111,817 to Clark et al., 5,526,808 to Kaminsky, and 5,642,734 to Ruben et al. are incorporated herein by reference.

Overview

An overview of one exemplary structure of the present invention will be followed by a discussion of its methods for hematocrit measurement.

Figure 1:
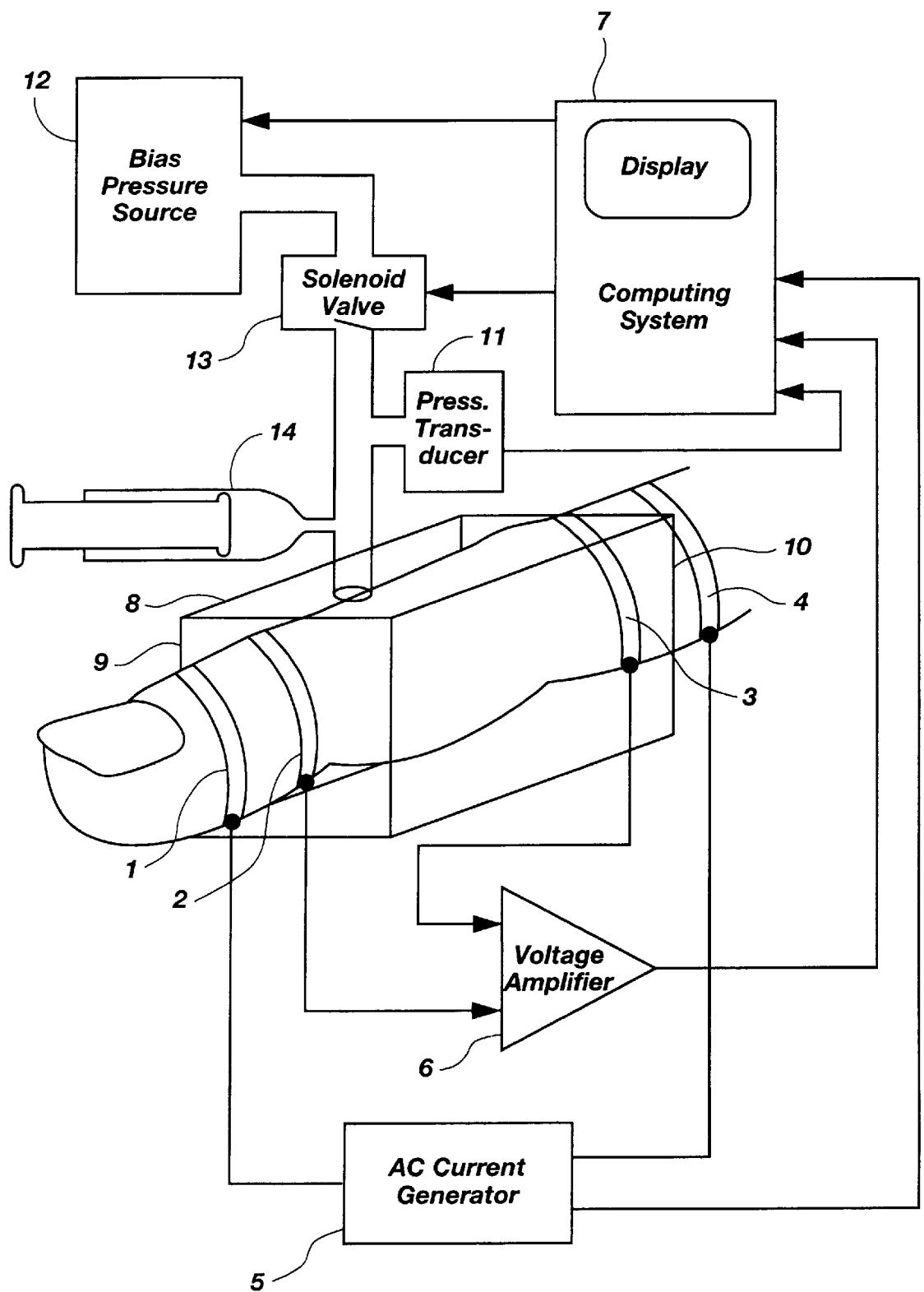
FIG. 1 is a block diagram of a hematocrit measurement system in accordance with this invention.

An embodiment of the present invention is shown in FIG. 1. In this embodiment, the pulsatile impedance and pulsatile pressure are measured in a chamber surrounding a patient's finger. Although a finger has been chosen as an exemplary body part to illustrate this embodiment, it is important to note that other body parts may be used.

An array of electrodes 1, 2, 3, and 4 is placed on the finger with the outer electrodes 1 and 4 separated as widely as possible and the inner electrodes 2 and 3 each separated by approximately 5.0 mm from the closest of outer electrodes 1 and 4 and separated from each other by a distance as far as possible but necessarily limited by the length of the finger.

The outer electrodes 1 and 4 are driven by an alternating current generator 5 which may be set to deliver a constant current at a frequency in the approximate range of 10 kHz to 200 kHz.

The optimum frequency for this system likely lies in the previously-mentioned range to achieve the goals of maximum current with no discernible neuromuscular stimulation and low phase difference between the current and voltage applied to the electrodes. While test results on an early prototype of this invention indicate that 100 kHz is appropriate for achieving satisfactory results, it is possible that another frequency may result in a more practical implementation.

The inner electrodes 2 and 3 are connected to the input of a high impedance voltage amplifier 6 which senses the voltage between these electrodes. Both the current generator 5 and the amplifier 6 are connected to a computing system 7, which combines these electrical signals with other signals from the pressure sensing apparatus (described below) to compute and display hematocrit. The computing system 7 also has the purpose of controlling the automated operation of the measurement apparatus. The details of the computing system 7 are not depicted in FIG. 1 or in the description of this invention because any of a number of configurations, including, but not limited to, an appropriately programmed PC-type computer with an analog-to-digital converter and an output port control interface, or a dedicated monitor, will suffice for performance of this function.

A sealed pressure chamber 8 surrounds the finger with airtight, pressure withstanding seals at its distal and proximal ends 9 and 10. These seals are located over, or in very close proximity to, the inner electrodes 2 and 3. The first purpose of this chamber 8 is to contain the air in the closed volume of the chamber around the finger so that small pulse pressure rises occur in the chamber 8 when blood from the arterial system of the patient's circulation is pulsed into the finger. The second purpose of this chamber 8 is to contain an externally applied bias pressure which causes blood vessels in the part of the finger that is enclosed by the chamber 8 to partially collapse. This partial collapse of the vessels results in greater blood flow into the finger on each cardiac pulse. In turn, the larger blood flow pulses, created as a result of the bias pressure, cause greater pressure pulses to occur within the chamber and greater voltage pulses to occur between the inner impedance sensing electrodes 2 and 3. It should be understood that the electrodes 1, 2, 3, and 4 may be integral with the chamber 8, or may be separate from the chamber 8 and applied to the finger independently of its insertion into the chamber.

A pressure transducer 11 is pneumatically connected to the pressure chamber 8 and electrically connected to the computing system 7 for sensing the bias pressure and the pulse pressure from which blood volume on each pulse is computed, and for transmitting signals representative of pressure to the computing system 7. Also connected pneumatically to the pressure chamber 8 is a bias pressure source 12 with a solenoid valve 13 controlled by the computing system 7. This valve 13 allows enough flow from the bias pressure source 12 to achieve the desired bias pressure, then shuts off to lock the bias pressure in. The pressure source 12 may be of any configuration having the ability to supply air at a pressure as high as approximately 200 mmHg above the ambient atmospheric pressure. The level of pressure supplied may optionally be controlled by the computing system 7.

Also connected to the pressure chamber 8 is a calibration source 14 which can inject a precisely known volume of air into the chamber 8 to calibrate the pressure change that represents a given volume. This calibration source 14 may be as simple as a small calibrated medical syringe, as shown in FIG. 1, which can be manually operated, or it can be a more complex device, controlled by the computing system 7, capable of producing precise volume pulses of close to the same magnitude as the cardiac pulses for dynamic calibration.

A Method of Measurement

It is known by those skilled in the art of physiological impedance measurements that the blood pulsed into a tissue space between a pair of sensing electrodes upon each heartbeat causes a pulsatile decrease in impedance. The change in impedance over time due to the heartbeat can be observed on an oscilloscope to obtain a picture called the impedance waveform. This waveform, when inverted and appropriately scaled, has approximately the same shape as does the change in blood volume over time due to the heartbeat. This similarity of waveforms suggests that the change of impedance is due to the change in volume and could be used to measure the volume change.

An equation relating the volume change, $\Delta V$, to the impedance change, $\Delta Z$, has been developed and has been reported by Geddes and Baker in "Principles of Applied Biomedical Instrumentation," second edition, John Wiley and Sons, New York (1975). This equation is:

$$\Delta V = \rho L^2 \Delta Z / Z_0^2 \qquad (1)$$

where $\Delta V$ is the change in blood volume at any point in time, $\Delta Z$ is the change of impedance at the same point in time, $\rho$ is the resistivity of the blood, L is the distance between the impedance sensing inner electrodes 2 and 3, and $Z_0$ is the baseline impedance at the beginning of each pulse.

The previously described equation (1) can be rearranged to solve for $\rho$, the resistivity, which we know to be dependent upon hematocrit:

$$\rho = \Delta V Z_0^2 / L^2 \Delta Z \qquad (2)$$

We now observe that all of the values needed for the computation of $\rho$ (i.e., $\Delta V$, $Z_0$, L, and $\Delta Z$) are measurable in the system previously described. Specifically, $\Delta V$ is measured by the pressure transducer 11 as the change of volume in the pressure chamber 8, $Z_0$ and $\Delta Z$ are measured by the voltage amplifier 6, and L is the measured distance between the inner sensing electrodes 2 and 3.

Having $\rho$, it is now straightforward to compute hematocrit. In their paper "The Specific Resistance of Blood at Body Temperature," Medical and Biological Engineering, 11:336–339 (1973), Geddes and Sadler have experimentally derived and reported mathematical relationships between blood resistivity ρ and hematocrit H in both simple algebraic and exponential forms. The algebraic form is:

$$\rho = (58 + 0.435H)/(1 - 0.01H) \quad (3)$$

where H is percent hematocrit. This can be solved for H in terms of ρ as:

$$H = (\rho - 58)/(0.01\rho + 0.435) \quad (4)$$

Having applied this last equation (4), using the value of ρ determined from the impedance and volume measurements, we now have hematocrit H, which was our original objective.

To obtain maximum accuracy in application of the equations shown above, a very accurate measurement of blood volume change (ΔV) should be made. This is accomplished by comparing, in the computing system 7, the pressure change within the chamber 8 on the finger against the pressure change that results from a known change in volume imposed by the calibration source 14. A calibration source 14 controlled by the computing system 7 can be adjusted to produce precisely controlled volume changes of approximately the same magnitude as those produced by the blood pulses. This method of calibration should produce the greatest accuracy of hematocrit measurement.

Optionally, the accuracy of both the impedance and direct volume measurements can be improved by producing larger arterial pulses in the finger. The imposition of a bias pressure in the chamber 8, having a magnitude above a substantial fraction of the systolic blood pressure at the finger, and preferably having a magnitude equal to the mean arterial blood pressure in the finger, has been shown experimentally to increase the pulse volume by as much as a factor of ten. The increase in pulse volume achieved by this means increases the accuracy of the hematocrit measurement by improving the signal-to-noise ratios on both the impedance and pressure channels going to the computing system 7. More importantly, the arterial component of the pulse volume becomes greater with respect to pulsatile volume changes in other vessels in the finger (such as the capillaries), which makes the derived hematocrit more nearly a true value.

Pattern Recognition Algorithms

Experiments have determined that the impedance pulse in the finger is often very weak compared to the pressure pulse, both of which are simultaneously measured in application of this invention. In detecting the impedance pulse by measuring the voltage on the inside electrode pair 2 and 3, it has been found that there is often a large noise voltage that obscures the signal and diminishes the accuracy of the measurement. In such situations, it is our practice to filter the noisy signal using an analog filter circuit or, alternatively, using a digital filtering algorithm, implemented in the computing system 7. One type of digital filter that may be used employs the assumption that the general shape of both the impedance pulse waveform and the pressure pulse waveform are the same. When this assumption is made, it follows that both signals must have the same frequency components. These facts, i.e., that both signals are of the same shape and frequency content, allow the use of adaptive filtering algorithms implemented either as matching filters in the time domain or frequency window filters in the frequency domain wherein the optimum filter parameters are derived from the characteristics of the relatively clean pressure signal waveform. In other words, the filtering algorithms use the relatively clean pressure signal waveform as a template for the relatively noisy impedance signal waveform to filter out noise.

Another Embodiment

The original method of hematocrit determination, described by Kaminsky in the '808 patent referenced above, was subject to limitations resulting from the very small blood volume pulses occurring in the finger and the noisy impedance signals. Application of the bias pressure method for enhancing the pulses, as taught by the present invention, as well as application of the filtering method described in the preceding paragraph, improves the accuracy of this two-frequency method, as well as any other multi-frequency method which depends upon the blood pulse for discrimination of the arterial blood impedance component. Any such implementation which uses a pressure chamber (or cuff) in conjunction with an electrode array to measure the pulse volume, to obtain a pressure pulse signal for deriving adaptive filter parameters, or to impose a bias pressure for enhancing the arterial pulse is considered to be within the scope of this invention.

Application of equation (2) described above to two separate frequencies allows us to obtain the following ratio:

$$(\rho_L/\rho_H) = (Z_L^2/Z_H^2) \cdot (\Delta Z_H/\Delta Z_L) \quad (5)$$

where $\rho_L$ is the resistivity of blood at the lower of the two frequencies, $\rho_H$ is the resistivity of the blood at the higher of the two frequencies, $Z_L$ is the baseline impedance for the low frequency, $Z_H$ is the baseline impedance for the high frequency, $\Delta Z_H$ is the change in impedance at a point in time for the high frequency, and $\Delta Z_L$ is the change in impedance at a corresponding point in time for the low frequency.

Notice that equation (5) offers the distinct advantage of canceling the geometric factors ΔV and L. By choosing a high frequency between 1 MHz and 10 MHz, the hematocrit H can be adequately represented as a function of $(\rho_L/\rho_H)$. The measurement of $(\rho_L/\rho_H)$ from equation (5) can be represented in terms of measurable voltages and currents by:

$$(\rho_L/\rho_H) = (\Delta \text{Volt}_H/\Delta \text{Volt}_L) \cdot (\text{Volt}_L^2/\text{Volt}_H^2) \cdot (I_H/I_L) \quad (6)$$

where ΔVolt, Volt, and I represent measurable pulse voltages, baseline voltages, and currents, respectively.

Since $I_H$ and $I_L$ are constant current sources which can be placed under instrument control, equation (6) can be simplified to:

$$(\rho_L/\rho_H) = C \cdot (\Delta \text{Volt}_H/V_H^2)/(\Delta \text{Volt}_L/V_L^2) \quad (7)$$

where $C = I_H/I_L$ is a known constant.

An In-Vivo Model for Relating $(\rho_L/\rho_H)$ to Hematocrit

A representation of $(\rho_L/\rho_P)$, as published by Geddes and Sadler ("The Specific Resistance of Blood at Body Temperature," Med. and Biol. Eng., 336–339, May, 1973), is given by:

$$(\rho_L/\rho_P) = [1 + (f-1) \cdot H]/(1-H) \quad (8)$$

where $\rho_P$ is the resistivity of plasma, and f is a form factor (determined by Geddes and Sadler to be 1.75 for human red blood cells when their orientation is random). The effect of frequency on blood resistivity is explained by noting that the red blood cell membrane behaves as an insulator at low frequencies, causing $\rho_L$ to be predictably higher with increasing hematocrit H. However, at frequencies of about 10 MHz and higher, the red blood cell membrane reactance is virtually eliminated, which causes the intracellular fluid to participate fully in the blood impedance measurement. This reduces the $\rho_H$ sensitivity to hematocrit H. The sensitivity of $\rho_H$ to hematocrit H would be virtually eliminated at frequencies of 10 MHz and higher if it were not for the fact that the resistivity of the intracellular fluid ($\rho_{RBS}$) varies somewhat from $\rho_P$.

Figure 3:
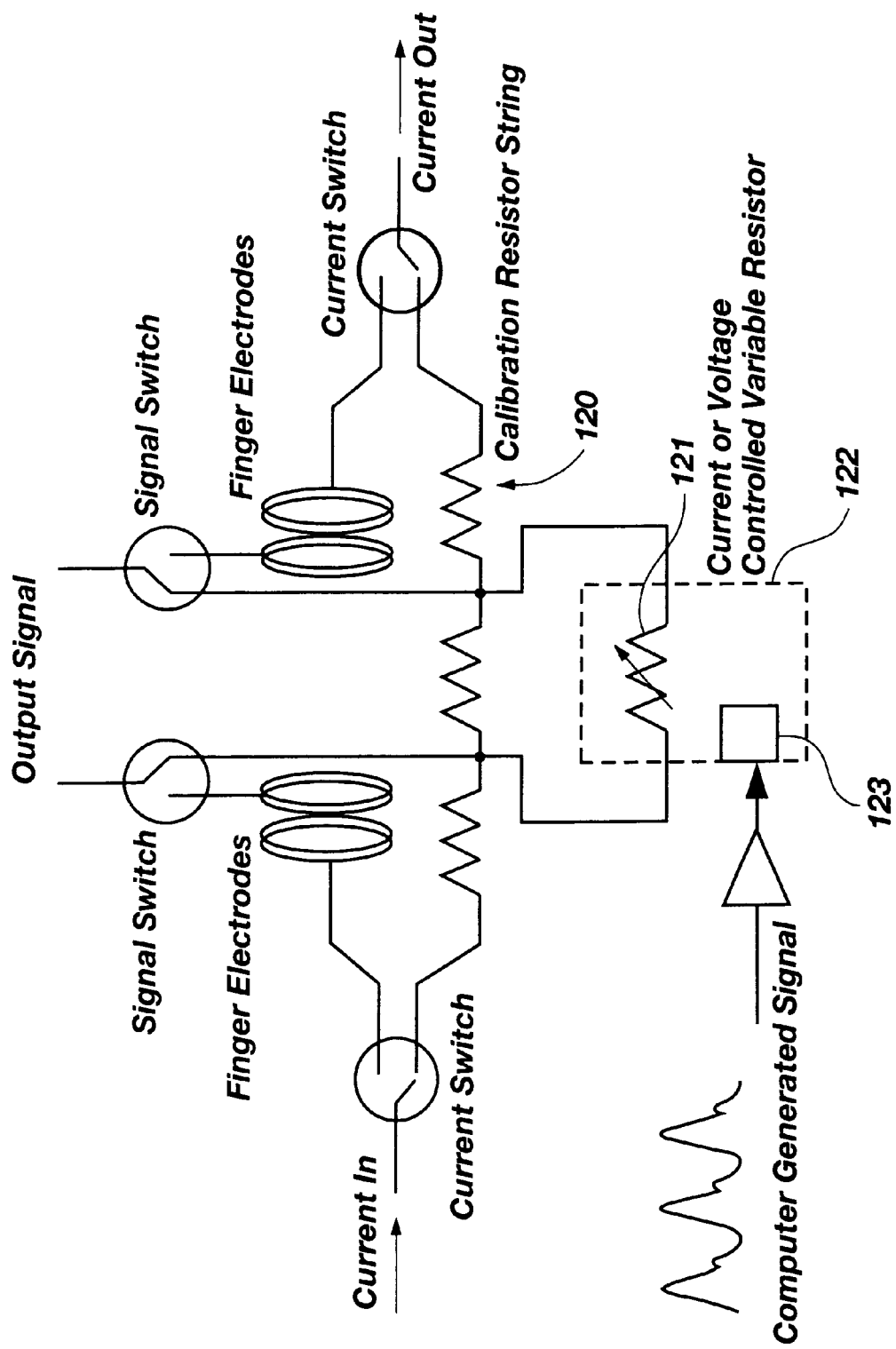
FIG. 3 is a diagram of a calibration system of the hematocrit measurement system of FIG. 2.

The theoretical foundation for expressing $\rho_H$ as a function of $\rho_P$, f, H, and $\rho_{RBC}$ was also reported by Fricke in "A Mathematical Treatment of the Electric Conductivity and Capacity of Disperse Systems," The Physical Rev., Vol. 24, 2nd Series, July–December, 1924, which we have extracted to give:

$$(\rho_H/\rho_P) = \{1 + [((af(e^{-bx}-c))/(1-x))-1] \cdot H\} / \{1 + [((af(e^{-bx}-c))x/(1-x))-1] \cdot H\} \quad (9)$$

where x is the red blood cell to plasma conductivity ratio, and a, b, and c are constants derived from the curves of FIG. 3 of Fricke, in which a=1.56, b=1.02, and c=0.36 (to conform with Geddes and Sadler, f is used in place of the value of $-\beta(x)$ for x=0). Note that equation (9) reduces to equation (8) for x=0, and reduces to unity as x approaches 1. It should also be noted that equation (9) applies at any frequency for which the value of x (the definition now includes the influence of the membrane on red blood cell conductivity) can be measured.

The $\rho_L/\rho_H$ ratio can now be determined by dividing equation (8) by equation (9), which gives:

$$(\rho_L/\rho_H) = [(1+(f-1)H)/(1-H)]\{1+[((af(e^{-bx}-c))x/(1-x))-1]H\}/\{1+[((af(e^{-bx}-c)/(1-x))-1]H\} \quad (10)$$

Figure 2:
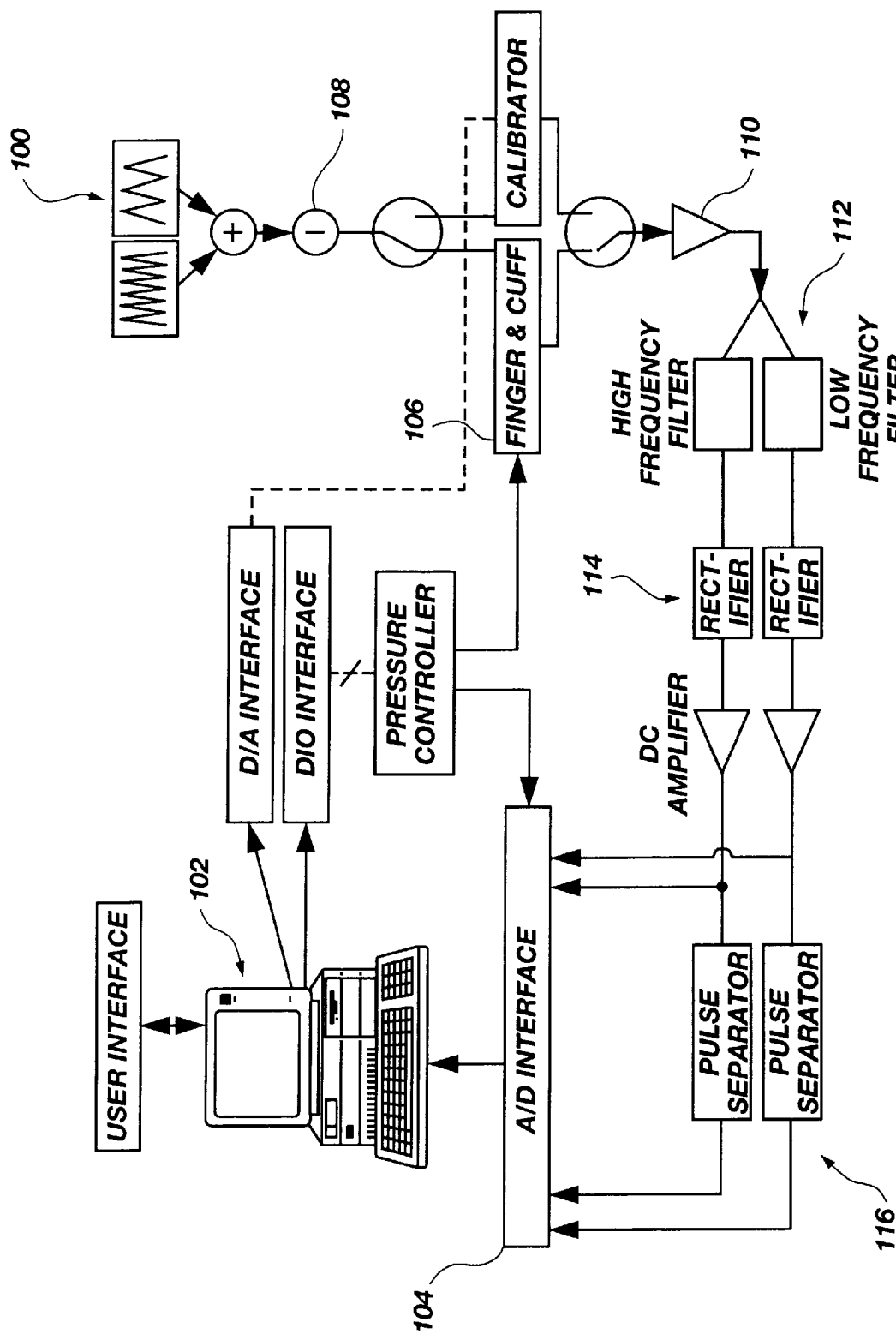
FIG. 2 is a block diagram of another hematocrit measurement system in accordance with this invention.

A block diagram of a two-frequency embodiment of the system is shown in FIG. 2. Waveform generators 100 for both 100 KHz and 10 MHz frequencies are laboratory instruments, although of course these signals would typically be generated by internal oscillators in a hematocrit measurement instrument to be used in the field. An exemplary host computer 102 is a fully equipped IBM-compatible system running general-purpose laboratory data processing software, custom configured for the computations required for these studies. In the field, the host computer 102 would typically comprise a dedicated processor with dedicated software or firmware.

The computer 102 is equipped with a multi-channel analog-to-digital converter 104 for monitoring the physiological signals of a patient. A finger 106 or, alternatively, a calibration resistor string (for experimental purposes), is driven by a constant amplitude current source 108 at both the low and high frequencies. The mixed voltage is picked up by the inner electrode pair (see FIG. 1), amplified by a sensing amplifier 110, then separated by a complementary pair 112 of low-pass and high-pass filters into two signals. The separated signals at both frequencies are then rectified with rectifiers 114 to provide DC signals at the baseline levels with the pulses superimposed on these DC levels. The pulses are then separated from the baseline voltages by subtracting a low-pass filtered signal from the pulse-containing signal using pulse separators 116. These pulses are then amplified to a level where they can be visualized on an oscilloscope display on the computer 102. The computer 102 monitors four signals: the two baselines and the two pulses. From these signals, the hematocrit calculations are performed using the equations described above.

Automated Calibration

An automated calibration system can enhance the accuracy of the hematocrit H measurement by compensating for drift in the electronics by periodically measuring the high and low frequency current ratios and the circuit gain ratios. To understand the calibration process, equation (7) is rewritten to give:

$$(\rho_L/\rho_H) = C' \cdot (\Delta \text{Volt}_H'/\Delta \text{Volt}_L')(\text{Volt}_L'^2/\text{Volt}_H'^2) \quad (11)$$

where the factor C' is an instrumentation calibration factor. The primes on the voltage parameters represent voltage measurements as opposed to true voltages existing at the measurement site. C', which includes the fixed current ratio $I_H/I_L$ and circuit gain ratios, then becomes:

$$C' = (I_H/I_L)(A_H/A_L)^2(DA_L/DA_H) \quad (12)$$

where $A_H$ and $A_L$ are the net amplification factors for the $V_H$ and $V_L$ channels, respectively; and $DA_H$ and $DA_L$ are the net pulse amplification factors for the respective frequencies. To the extent that the net amplification factors are linear (which include the sensing amplifier 110, filters 112, and rectifiers 114), the system can be calibrated by a single adjustment of the calibration factor C'. One method to obtain a value for C' uses a string of three resistors, connected either manually or by switching after the calibration is automated, in place of the finger. This puts the resistor string (shown as 120 in FIG. 3) in the circuit.

Referring once again to FIG. 2, the constant amplitude current source 108 pushes the fixed currents at both frequencies through the resistors 120 (of FIG. 3) and the sensing amplifier 110 receives the differential signal from the two ends of the center resistor. To produce a pulse analogous to the blood-caused impedance pulse in the finger, a fourth resistor 122 of FIG. 3, which is larger and variable, can be placed in parallel with the center resistor and varied by some means One embodiment for the parallel resistor 122 is a semiconductor photoresistor 121 enclosed in an opaque cylinder, which also contains a light emitting diode 123. The current drive to the diode 123 will be varied in the shape of an arterial impedance pulse from a signal generated in the computer 102.

This configuration and method of pulse generation assures that both the base impedances and impedance pulses are of the same amplitude at both the high and low frequencies. Once equality of both base and pulse impedances is assured, it is possible to measure all the parameters of equation (11), on the same electronics that measure the finger parameters, with $(\rho_L/\rho_H) = 1.0$, and solve for C' by:

$$C' = (\Delta \text{Volt}_L'/\Delta \text{Volt}_H')(\text{Volt}_H'^2/\text{Volt}_L'^2) \quad (13)$$

The reader should note that various mathematical terms (e.g., product and ratio) appear in some of the appended claims. The inventors have used the term "effective" in the claims in association with these mathematical terms to clarify the fact that this invention includes within its scope, among other things, all systems and methods by which hematocrit is calculated using the variables and constants as described herein. The invention is not limited to any particular system or method for correlating hematocrit to these variables and constants, nor is it limited to any particular order or form of calculation. In other words, the invention includes within its scope all systems and methods for calculating hematocrit from the variables and constants described herein which "effectively" calculate hematocrit in the manner described herein, no matter the actual method by which the calculation is performed. Also, it should be understood that the phrase "effectively determining a ratio," for example, is meant to include, not exclude, the act of actually determining the ratio.

Although this invention has been described with reference to particular embodiments, the invention is not limited to these described embodiments. For example, it should be understood that the signal enhancing effect described above as being associated with the application of pressure to the finger or other body part under test can be achieved in any of the embodiments disclosed herein. Thus, the invention is limited only by the appended claims, which include within their scope all equivalent devices and methods that operate according to the principles of the invention as described.

We claim:

1. A method of measuring the hematocrit of blood perfusing a living body part, the method comprising:
   driving first and second alternating currents of different frequencies between separate points on the body part;
   monitoring first and second signals induced in the body part by the respective first and second currents;
   generating first and second pulsatile signals and first and second baseline signals from the respective first and second induced signals; and
   determining the hematocrit of the blood from the first and second pulsatile signals and the first and second baseline signals.

2. The method of claim 1, wherein driving the alternating currents comprises driving the first and second alternating currents at frequencies of 100 KHz and 10 MHz, respectively, between separate points on the body part.

3. The method of claim 1, further comprising applying an external bias pressure to the body part proximate the separate points between which the currents are driven to enhance a signal-to-noise ratio of the first and second induced signals.

4. The method of claim 3, wherein applying the external bias pressure comprises applying the pressure using one of a chamber and a cuff.

5. The method of claim 3, further comprising regulating the application of the external bias pressure to the body part in accordance with at least one of the pulsatile and baseline signals.

6. The method of claim 1, wherein driving the currents comprises driving the currents between electrodes positioned on an external surface of the body part.

7. The method of claim 1, wherein the act of monitoring the first and second induced signals comprises monitoring first and second induced voltages.

8. The method of claim 1, wherein generating the pulsatile and baseline signals comprises separating pulsatile components of the induced signals from baseline components of the induced signals.

9. The method of claim 1, wherein determining the hematocrit includes effectively determining the ratio of: the product of the second pulsatile signal and the square of the first baseline signal to the product of the first pulsatile signal and the square of the second baseline signal.

10. The method of claim 1, wherein determining the hematocrit includes determining the hematocrit from the pulsatile signals, the baseline signals, and a constant, wherein the method further comprises effectively calibrating the constant under predetermined calibration conditions in accordance with the ratio of: the product of the first pulsatile signal and the square of the second baseline signal to the product of the second pulsatile signal and the square of the first baseline signal.

11. The method of claim 10, wherein effectively calibrating includes driving the first and second alternating currents through a resistor network having parallel fixed and variable resistance paths.

12. The method of claim 11, wherein driving the currents through the resistor network includes varying resistance of the variable resistance path in accordance with an artificial arterial impedance pulse signal.

13. The method of claim 12, wherein the variable resistance path includes a photoresistor, wherein varying the resistance of the variable resistance path comprises varying resistance of the photoresistor by driving a light emitting diode proximate the photoresistor with the artificial arterial impedance pulse signal.

14. The method of claim 1, further comprising:
   measuring a change in a volume of the blood over time; and
   filtering noise from the induced signals using a template derived from the measured change.

15. The method of claim 14, wherein measuring the change in the volume of the blood over time includes reading a pressure transducer coupled to one of a pressurized chamber and cuff positioned proximate the body part.

16. A system for measuring the hematocrit of blood perfusing a living body part, the system comprising:
   circuitry for driving first and second alternating currents of different frequencies between separate points on the body part;
   circuitry for monitoring first and second signals induced in the body part by the respective first and second currents;
   circuitry coupled to the monitoring circuitry for generating first and second pulsatile signals and first and second baseline signals from the respective first and second induced signals; and
   circuitry coupled to the generating circuitry for determining the hematocrit of the blood from the first and second pulsatile signals and the first and second baseline signals.

17. The system of claim 16, further comprising an external bias pressure device for applying an external bias pressure to the body part.

18. The system of claim 17, wherein the external bias pressure device comprises one of a chamber and a cuff.

19. The system of claim 17, further comprising an apparatus coupled to the external bias pressure device and the determining circuitry for regulating the application of the external bias pressure to the body part in accordance with at least one of the pulsatile and baseline signals.

20. The system of claim 16, wherein the driving circuitry includes electrodes positioned on an external surface of the body part.

21. The system of claim 17, wherein the electrodes are integrated into the external bias pressure device.

22. The system of claim 16, wherein the monitoring circuitry includes:
   electrodes positioned on an external surface of the body part; and
   circuitry coupled to the electrodes for monitoring first and second voltages induced between the electrodes by the first and second currents.

23. The system of claim 16, wherein the generating circuitry includes circuitry for separating the pulsatile components of the induced signals from the baseline components of the induced signals.

24. The system of claim 16, wherein the determining circuitry includes circuitry for effectively determining the ratio of: the product of the second pulsatile signal and the square of the first baseline signal to the product of the first pulsatile signal and the square of the second baseline signal.

25. The system of claim 16, wherein the determining circuitry includes:
   circuitry for determining the hematocrit from the pulsatile signals, the baseline signals, and a constant; and
   circuitry for effectively calibrating the constant under predetermined calibration conditions in accordance with the ratio of: the product of the first pulsatile signal and the square of the second baseline signal to the product of the second pulsatile signal and the square of the first baseline signal.

26. The system of claim 25, wherein the calibrating circuitry includes a resistor network having parallel fixed and variable resistance paths.

27. The system of claim 26, wherein the calibrating circuitry further includes circuitry for varying a resistance of the variable resistance path in accordance with an artificial arterial impedance pulse signal.

28. The system of claim 27, wherein the variable resistance path of the resistor network includes a photoresistor and a light emitting diode proximate the photoresistor, wherein the varying circuitry comprises circuitry for varying a resistance of the photoresistor by driving the light emitting diode with the artificial arterial impedance pulse signal.

29. The system of claim 16, further comprising:
   an apparatus for measuring a change in the volume of the blood over time; and
   circuitry coupled to the measuring apparatus for filtering noise from the induced signals using a template derived from the measured change.

30. The system of claim 29, wherein the measuring apparatus includes:
   a pressure transducer; and
   at least one of a chamber and a cuff positioned on the body part and coupled to the pressure transducer.

* * * * *